United States Patent [19]
Olson

[11] Patent Number: 5,620,413
[45] Date of Patent: Apr. 15, 1997

[54] COMBINATION ANKLE BRACE AND WRAP

[76] Inventor: Donaebill G. Olson, 15832 Tradewind Dr., Spirit Lake, Iowa 56101

[21] Appl. No.: 502,571

[22] Filed: Jul. 14, 1995

[51] Int. Cl.⁶ ........................................ A61F 5/00
[52] U.S. Cl. ............................... 602/65; 602/27
[58] Field of Search .............. 602/5, 23, 27–29, 602/61, 65, 66

[56] References Cited

U.S. PATENT DOCUMENTS

| | | |
|---|---|---|
| D. 326,948 | 6/1992 | Williams et al. . |
| 3,028,861 | 4/1962 | Shapiro ................................ 602/65 |
| 3,506,000 | 4/1970 | Baker . |
| 3,515,136 | 6/1970 | Baker . |
| 3,674,023 | 7/1972 | Mann . |
| 4,133,311 | 1/1979 | Karczewski ............................. 602/65 |
| 4,280,488 | 7/1981 | Polsky et al. ......................... 602/65 X |
| 4,367,733 | 1/1983 | Stromgren . |
| 4,621,648 | 11/1986 | Ivany .................................. 602/65 X |
| 4,630,600 | 12/1986 | Spencer et al. . |
| 4,727,863 | 3/1988 | Nelson ................................. 602/65 X |
| 4,729,370 | 3/1988 | Kallassy .................................. 602/65 |
| 4,753,228 | 6/1988 | Selner et al. . |
| 5,067,486 | 11/1991 | Hely . |
| 5,139,479 | 8/1992 | Peters . |
| 5,151,081 | 9/1992 | Williams . |
| 5,464,384 | 11/1995 | Cromartie ............................... 602/27 |

*Primary Examiner*—Linda C. Dvorak
*Attorney, Agent, or Firm*—Zarley, McKee, Thomte, Voorhees & Sease

[57] ABSTRACT

A combination ankle brace and wrap is comprised of a compression support sleeve adapted to fit over the foot of the user. A non-elastic strap is secured to the pressure support sleeve and wraps around the plantar of the foot and back around the ankle forming a figure eight configuration. Two pressure release pads are disposed on the compression support sleeve parallel to each other forming a channel along the Achilles tendon of the user to provide a redistribution of the forces from the strap near the Achilles tendon.

14 Claims, 2 Drawing Sheets

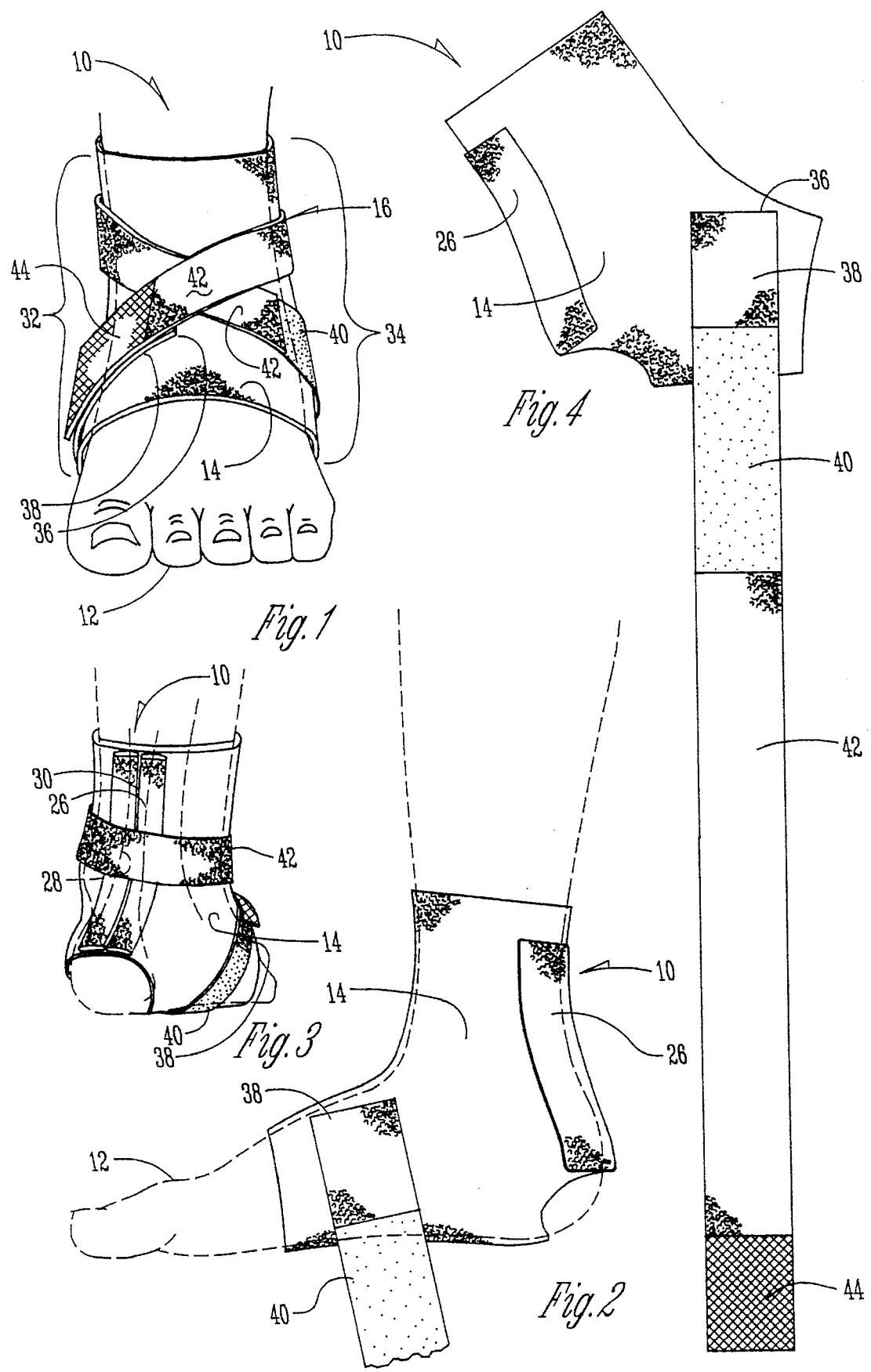

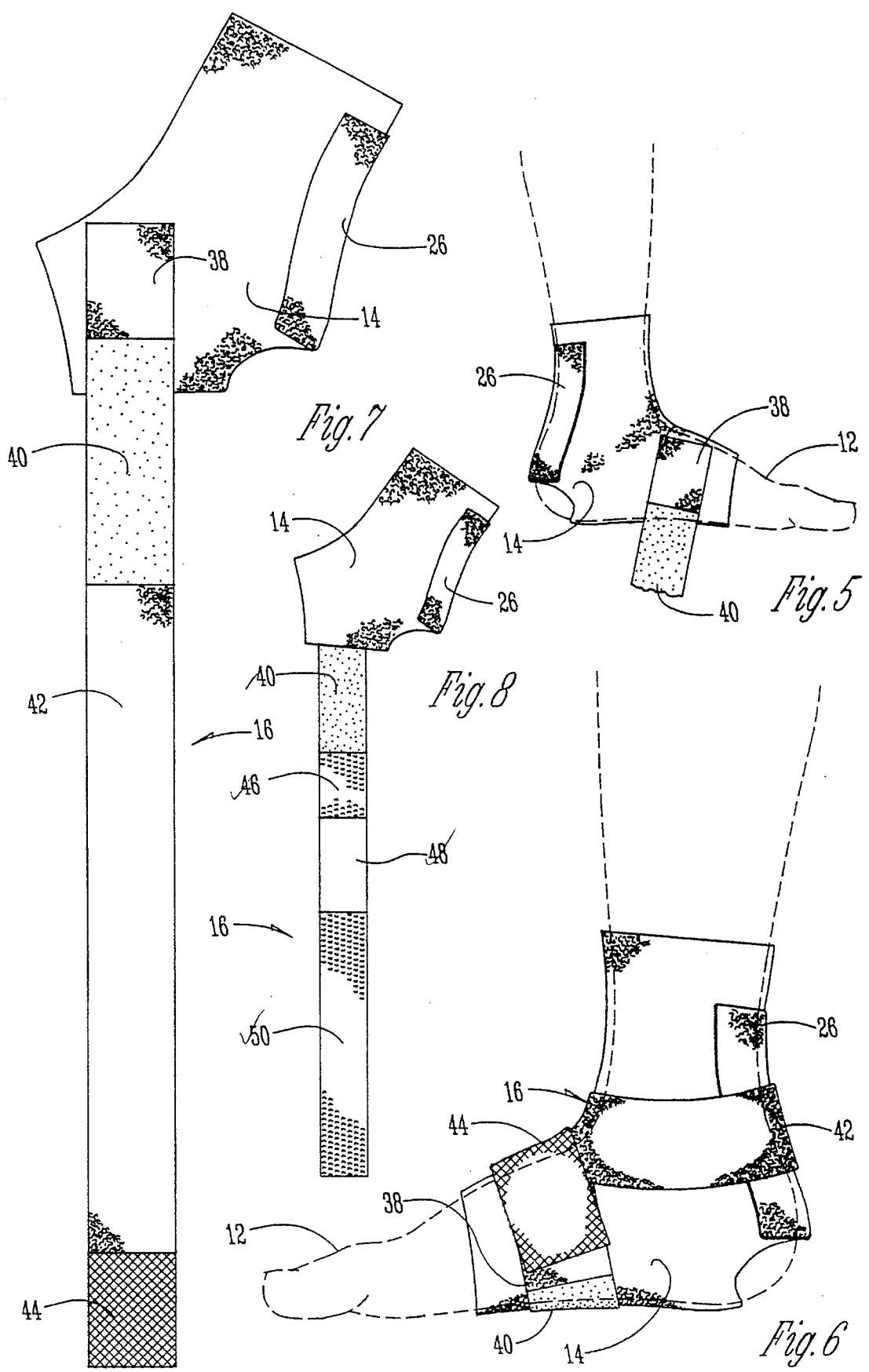

COMBINATION ANKLE BRACE AND WRAP

BACKGROUND OF THE INVENTION

1. Field of the Invention

The present invention relates to a combination ankle brace and wrap. More particularly, the present invention relates to an ankle brace and wrap comprised of a compression support sleeve, a non-elastic strap, and a pair of pressure release pads.

2. Problems in the Art

There are a variety of ways in the prior art to provide support or bracing for an ankle. For example, it is well known and accepted to tape the ankles of athletes to provide support to the ankles. Other types of prior art supports include elastic wrappings, lace up braces, or slip on braces with straps. However, all of these prior art ankle support devices have various disadvantages.

Perhaps the most common type of ankle support comes from taping the ankle. A taped ankle can result in excessive pressure on the ankle as well as being uncomfortable for the user. Tape can also restrict the freedom of movement which reduces the range of performance which may restrict performance. In addition, a qualified person with the expertise is required to tape an ankle. Also, the tape can loosen during use. Another disadvantage of tape is that it can only be used once and then is thrown away.

A number of reusable ankle supports are known in the art. The prior art reusable ankle supports typically provide limited bracing of the ankle. Some apply considerable constriction to the ankle.

Prior art ankle supports using elastic materials are also common. However, the elastic material has been found to provide relatively little bracing in ankle supports. Most reusable ankle supports are heavy, uncomfortable, and have a relatively short life span.

Non-elastic rigid strip ankle supports can cause pain to the Achilles tendon of the wearer. When a strap or other fastening means is used to brace an ankle, the strap can cause excessive pressure on the Achilles tendon because of the particular sharp angle as compared to the anatomical contours of the foot.

Prior art ankle supports also can reduce the circulation in the foot of the wearer.

FEATURES OF THE INVENTION

A general feature of the present invention is the provision of a combination ankle brace and wrap.

A further feature of the present invention is the provision of a combination ankle brace and wrap that includes a compression support sleeve and a non-elastic rigid strap.

A further feature of the present invention is the provision of a combination ankle brace and wrap having a pair of pads parallel to each other in the proximity of the wearer's Achilles tendon to provide redistribution of the tension of the strap.

A further feature of the present invention is the provision of a combination ankle brace and wrap having a non-elastic strap that can be wrapped around the foot and ankle to provide support to the ankle.

A further feature of the present invention is the provision of a combination ankle compression support sock and wrap with hook fasteners that provide continuous adhesion to the sock with the terminal hook portion of the strap being secured by a loop pad on the anterior medial surface of the compression support sock.

A further feature of the strap of the present invention is the provision of a non-restrictive comfort zone as it crosses over the extensor hallicus longus and extensor digitorum longus tendons in the anterior area of the ankle. This allowance permits full plantar and dorsal flexion without any binding or restriction.

A further feature of the present invention is the provision of a combination ankle brace and wrap having hook and loop or hook fasteners for natural continuous securing of the strap in the braced position and a touch down pad to lock strap at terminal end.

A further feature of the present invention is the provision of the strap having an anterior comfort zone as it crosses over the extension hallicus and digitorum longus tendons of the foot to allow greater comfort in the full range of plantar and dorsal flexion of the foot.

A further feature of the present invention is the provision of a combination ankle brace and wrap that it easily adjusted by the wearer.

These as well as other features of the present invention will become apparent from the following specification and claims.

SUMMARY OF THE INVENTION

The combination ankle brace and wrap of the present invention is a quick and simple device which provides a non yielding support restricting ankle inversion. The brace includes a compression support sleeve adapted to fit over the foot of a user and a non-elastic strap secured to the sleeve and adapted to wrap around the foot and ankle in a figure eight configuration. The ankle brace also includes a pair of pressure release pads disposed parallel to each other forming a channel along the user's Achilles tendon to provide a redistribution of the tension from the strap which occurs near the Achilles' tendon.

BRIEF DESCRIPTION OF THE DRAWINGS

FIG. 1 shows a front view of the present invention as worn by a user.

FIG. 2 shows a side view of the present invention with the non-elastic strap unwrapped.

FIG. 3 is a rear view showing the pressure release pads.

FIG. 4 is a plan view of the present invention before it is inserted on a foot.

FIG. 5 is a side view similar to FIG. 2 except for a left foot.

FIG. 6 is a side view of the present invention with the strap wrapped around the ankle in a figure eight configuration.

FIG. 7 is a view like FIG. 4 except for the right foot.

FIG. 8 is a plan view of the present invention showing the opposite side of FIG. 4.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention.

FIG. 1 shows a combination ankle brace and wrap 10 inserted over the foot 12 of user. The ankle brace 10 is comprised of a compression support sleeve 14 and a non-elastic rigid strap 16. The compression support sleeve 14 and non-elastic rigid strap 16 as described below provide a non-yielding support restricting ankle inversion. This is a result of the placement and directional forces of the strap 16 with the foot positioned in maximum dorsi flexion. The compression support sleeve 14 is adapted to slide over the foot 12 of the user as shown in FIGS. 1 and 2 to provide a tight fit around the ankle. The compression support sleeve 14 is comprised of an elastic firm stitched material which provides support around the foot and around the lateral and medial malleolus of the ankle. The heel and front part of the foot are exposed when the sleeve is inserted over the foot (FIG. 2).

The figures show the present invention for both the left and right foot of a user. FIGS. 1, 3, 4, 5 and 8 show a brace adapted for a left foot while FIGS. 2, 6, and 7 show a brace adapted for a right foot.

The compression support sleeve 14 is designed with two pressure release pads 26 located on the medial and lateral side of the Achilles tendon 28 (shown by dashed lines in FIG. 3) to protect the Achilles tendon. As shown in FIGS. 2 and 3, the pressure release pads 26 are generally parallel to each other and form a channel 30 between the two pads. When the brace 10 is inserted over the foot of the user, the channel 30 will generally correspond to the user's Achilles tendon 28 (FIG. 3). The pads 26 provide a redistribution of the tension from the strap 16 which occurs at the site of the Achilles tendon because of the particular sharp angle as compared to the anatomical contours of the foot which flow less obstruently in the figure eight application of the strap. The pads 26 also provide a critical external protection to both the medial and lateral aspect of the Achilles tendon. Both the compression support sleeve 14 and the pressure release pads 26 have a loop-type surface for engaging with a hook surface.

The ankle brace 10 has a medial side 32 and a lateral side 34 as shown in FIG. 1. The first end 36 of the non-elastic strap 16 is secured to the medial side 32 of the compression support sleeve 14. After the compression support sleeve 14 is inserted over the user's foot, the strap 16 is wrapped along the plantar surface of the foot to the lateral side 34 of the sleeve 14 as shown in FIG. 1. The strap 16 is then wrapped over the top of the foot and around to the back of the ankle. The strap 16 is finally wrapped back to the medial side 32 of the sleeve where the first end 36 of the strap 16 is secured to the sleeve 14, generally forming a figure eight configuration (FIGS. 1 and 6). The strap 16 is secured in the figure eight position by a number of hook and loop fasteners as described below.

FIGS. 4, 7, and 8 show the ankle brace 10 before it is inserted over the user's foot. The strap 16 includes various portions and surfaces as follows. A first portion 38 is secured to the compression support sleeve 14 and includes a loop surface which faces outward relative to the compression support sleeve 14. A second portion 40 of the strap is preferably a cotton-canvas type of material. When the brace 10 is inserted over the foot in the manner described above, the second portion 40 of the strap will be disposed along the plantar surface of the foot. The remainder of the strap 16 is nylon and comprises a third portion. As shown in FIGS. 4 and 7, the third portion includes outside surfaces 42 and 44. Surface 42 is a loop surface while surface 44 is neither a loop or a hook surface. When the brace 10 is inserted on the foot, the loop surface 42 is be disposed over the top of the foot and around the back of the ankle (FIGS. 1 and 6). FIG. 8 shows the opposite side of the strap shown in FIG. 4 which is the inside surface. The inside surface of the third portion of the strap 16 includes surfaces 46, 48, and 50. Surfaces 46 and 50 are hook surfaces which, when the brace 10 is inserted, secure the brace 10 the foot. Surface 48 comprises an extension tendon comfort zone. Surface 48 has neither a hook or loop surface making it softer than surfaces 46 and 50. The comfort zone 48 is positioned such that it crosses over the extensor hallicus tendons in front of the foot to allow greater comfort and is non-restricting to full range of plantar and dorsal flexion of the foot.

When the sleeve 14 is inserted over the foot and the strap 16 is in the figure eight configuration shown in FIGS. 1 and 6, the loop surface 42 of the strap will be positioned on the top of the foot and around the ankle with the loop surface facing outward from the sleeve 14. When the strap 16 is brought around the ankle and back over the top of the foot (FIG. 1), the hook surfaces 46 and 50 will come into engagement with the loop surface 42, the loop surface on the pressure release pads 26, and the surface of the sleeve 14 securing the strap in place.

The lateral ankle brace and support of the present invention is a quick and non complicated device. The strap can be easily adjusted when causing discomfort to the user as a result of too tight or loose of an application. The strap can be tailored to the individual user by cutting excessive length off during the initial fitting. The brace and support can be made to be any size depending on the user. The reusable lateral ankle support can be washed as frequently as desired.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. An ankle brace comprising:

an elastic compression support sleeve adapted to fit over the foot of a user, said sleeve having a medial, lateral, and a back side and upper and lower portions;

a non-elastic strap having a first and second end, said first end coupled to the compression support sleeve proximate the lower portion of the compression support sleeve, said strap and sleeve including a hook and loop fastener for securing the strap around the compression support sleeve when the sleeve is fitted over the foot of the user; and a first and second pressure release pad each disposed on the back side of the sleeve generally parallel to each other defining a channel, the channel being disposed in the proximity of the Achilles tendon of the user and having a width which is at least as narrow as the Achilles tendon of the user.

2. The ankle brace of claim 1 wherein the non-elastic strap is adapted to be wrapped around the foot and the ankle generally forming a figure eight configuration.

3. The ankle brace of claim 2 wherein the non-elastic strap is adapted to be wrapped in the figure eight configuration by being wrapped around the plantar surface of the foot from the medial side to the lateral side and then around the medial side of the ankle around the back of the ankle to the lateral side of the ankle and back to the medial side of the foot.

4. The ankle brace of claim 1 wherein the non-elastic strap is positioned over a portion of the first and second pressure release pads when the strap is secured around the compression support sleeve.

5. The ankle brace of claim 4 wherein the pressure release pads include a hook and loop fastener for fastening to a mating hook and loop fastener of the non-elastic strap to prevent the strap from sliding along the pressure release pads.

6. The ankle brace of claim 2 wherein the portion of the non-elastic strap wrapped around the plantar surface of the foot is comprised of a canvas material.

7. The ankle brace of claim 1 wherein the compression support sleeve is comprised of a firm stitched material.

8. The ankle brace of claim 2 wherein said non-elastic strap includes a portion on the inside surface of the strap which, when secured to the sleeve is disposed proximate the extensor hallicus tendons of the user, wherein said portion does not include a hook and loop fastener.

9. The ankle brace of claim 8 wherein said portion is softer than the remainder of the non-elastic strap.

10. The ankle brace of claim 1 wherein the ankle brace comprises no more than one non-elastic strap.

11. An ankle brace comprising:

a compression support sleeve adapted to fit over the foot of a user, said sleeve having a medial, lateral, and a back side, and upper and lower portions;

a non-elastic strap having a first and second end, said first end coupled to the compression support sleeve proximate the lower portion of the compression support sleeve, said strap and sleeve including a hook and loop fastener for securing the strap around the compression support sleeve when the sleeve is fitted over the foot of the user, wherein the non-elastic strap is adapted to be wrapped around the foot and the ankle generally forming a figure eight configuration, and wherein the portion of the non-elastic strap wrapped around the plantar surface of the foot is comprised of a canvas material; and a first and second pressure release pad each disposed on the back side of the sleeve generally parallel to each other defining a channel in the proximity of the Achilles tendon of the user.

12. A method of supporting an ankle of a user comprising the steps of:

providing an elastic compression support sleeve having a medial, lateral, and a back side and upper and lower portions;

providing a non-elastic strap coupled to the compression support sleeve proximate the lower portion of the compression support sleeve, said strap including a hook and loop fastener for securing the strap to the compression support sleeve when the sleeve is fitted over the foot of the user;

providing a first and second pressure release pad each disposed on the back side of the sleeve generally parallel to each other defining a channel;

placing the compression support sleeve over the ankle of the user such that the channel is parallel to and in the proximity of the Achilles tendon of the user so that the pressure release pads redistribute any tension from the strap at the site of the Achilles tendon;

wrapping the strap around the foot and ankle to provide support to the ankle; and securing the strap to the compression support sleeve.

13. The method of claim 12 wherein the step of wrapping the strap around the foot and ankle is performed such that the strap is wrapped in a figure eight configuration.

14. The method of claim 12 wherein no more than one non-elastic strap is provided.

* * * * *